United States Patent
Kulshrestha et al.

(10) Patent No.: US 10,385,002 B2
(45) Date of Patent: Aug. 20, 2019

(54) PROCESS FOR MAKING ESTERS OF 2-ACETOXYALKANOIC ACIDS USING A 3,6-DIALKYL-1,4-DIOXANE-2,5-DIONE OR POLY-(ALPHA-HYDROXYALKANOIC ACID) AS A STARTING MATERIAL

(71) Applicant: NatureWorks LLC, Minnetonka, MN (US)

(72) Inventors: Aman Kulshrestha, Plymouth, MI (US); Joseph David Schroeder, Minneapolis, MN (US)

(73) Assignee: NatureWorks LLC, Minnetonka, MN (US)

( * ) Notice: Subject to any disclaimer, the term of this patent is extended or adjusted under 35 U.S.C. 154(b) by 0 days.

(21) Appl. No.: 15/120,498

(22) PCT Filed: Feb. 23, 2015

(86) PCT No.: PCT/US2015/017129
§ 371 (c)(1),
(2) Date: Aug. 19, 2016

(87) PCT Pub. No.: WO2015/127374
PCT Pub. Date: Aug. 27, 2015

(65) Prior Publication Data
US 2017/0066708 A1    Mar. 9, 2017

Related U.S. Application Data

(60) Provisional application No. 61/943,993, filed on Feb. 24, 2014.

(51) Int. Cl.
*C07C 67/02* (2006.01)
*C07C 69/67* (2006.01)

(52) U.S. Cl.
CPC .................................. *C07C 67/02* (2013.01)

(58) Field of Classification Search
None
See application file for complete search history.

(56) References Cited

U.S. PATENT DOCUMENTS

| | | | |
|---|---|---|---|
| 1,927,295 A | 9/1933 | Powers | |
| 2,342,613 A | 4/1941 | Hansley | |
| 6,992,209 B2 | 1/2006 | Lilga | |
| 2012/0078004 A1* | 3/2012 | Fruchey | C07C 67/02 560/211 |

FOREIGN PATENT DOCUMENTS

| | | | |
|---|---|---|---|
| CN | 102675102 | * | 9/2012 |
| WO | 2014/045036 A | | 3/2014 |

OTHER PUBLICATIONS

Rehberg, Industrial and Engineering Chemistry vol. 36, #5, pp. 469-472 (1944).
Filchione et al., Industrial and Engineering Chemistry vol. 36, #5, pp. 472-475 (1944).
Rehberg, JACS vol. 67, pp. 56-66 (1945).
Vu et al., Fluid Phase Equilibria 236 (235) 125-135, (2005).

* cited by examiner

*Primary Examiner* — Amy C Bonaparte

(57) ABSTRACT

2-Acetoxyalkanoic acid esters are made in a reaction of a 3,6-dialkyl-1,4-dioxane-2,5-dione or a poly($\alpha$-hydroxyalkanoic acid), an acetate ester and an alcohol or phenol in the presence of a transesterification catalyst. Unlike previous methods for making 2-acetoxyalkanoic acid esters, this process proceeds in high yield and high selectivity to the desired product.

11 Claims, No Drawings

PROCESS FOR MAKING ESTERS OF 2-ACETOXYALKANOIC ACIDS USING A 3,6-DIALKYL-1,4-DIOXANE-2,5-DIONE OR POLY-(ALPHA-HYDROXYALKANOIC ACID) AS A STARTING MATERIAL

This invention relates to a method for making esters of 2-acetoxyalkanoic acids.

Methyl 2-acetoxypropionate (MAP) is a chemical intermediate of some interest because it can be pyrolyzed to form methyl acrylate and acetic acid. Methyl acrylate is useful as a monomer that can be polymerized to form poly(methylacrylate), and can be converted easily to acrylic acid or other acrylate esters. Therefore, an economical synthetic route to making MAP would have great value.

MAP can be produced in one or more steps starting from lactic acid. Therefore, acrylic acid and acrylate esters can be produced using lactic acid as a starting material. Lactic acid is made in large volumes via fermentation processes and so is both inexpensive and widely available. Acrylic acid and its esters could be produced quite inexpensively if there were an efficient process for converting lactic acid to MAP. However, the known synthetic routes from lactic acid to MAP have been plagued by low conversions and the production of large amounts of unwanted by-products. See, for example, Rehberg et al., *Industrial and Engineering Chemistry* Vol. 36, pp. 469-472 (1944); Filachione et al., *Industrial and Engineering Chemistry* Vol. 36 pp. 472-475 (1944); Rehberg et al., *JACS* vol. 67, pp. 56-56 (1945) and U.S. Pat. No. 6,992,209.

A significant contributor to the poor yield and selectivity is the presence of water in the system. Water is always present in the prior art processes, because it is produced in the reaction. More water is almost always carried into the process with the lactic acid, which is difficult to produce in anhydrous form. The water hydrolyzes the various ester compounds (including the product) back to the starting materials or other acids such as acetic acid. These acids are also corrosive to many metals, so the reaction vessel and associated equipment would need to be made of special alloys. In addition, the water forms an azeotrope with methyl lactate, which is an impurity that forms in large quantities in this reaction. It is difficult and expensive to separate the methyl lactate from the water to recover and recycle the lactic acid values.

Removing water from lactic acid leads to other problems, including the oligomerization of the lactic acid. For this reason, commercially available concentrated lactic acid syrups contain large amounts of low molecular weight oligomers that typically have at least one terminal carboxyl group, as well as a significant amount of residual water. The oligomers typically have degrees of polymerization of mainly 2 to 5. For example, in a typical commercially available 85% lactic acid syrup, 20% or more of the lactic acid is in the form or these low molecular weight oligomers. The combined concentrations of water and carboxyl groups in these highly concentrated lactic acid products often exceeds 10 moles/kg. The presence of the residual water and these low molecular weight oligomers in concentrated lactic acid syrups leads to diminished yields and unwanted by-products. It is not practical to provide a nearly anhydrous monomeric lactic acid starting material.

Two molecules of lactic acid can be dehydrated to form a cyclic dimer, which is commonly known as lactide. Unlike lactic acid, lactide can be produced in substantially anhydrous form. Therefore, another possible approach to making MAP starts with lactide rather than lactic acid or lactic acid ester. Such an approach is described schematically in FIG. 5 of US 2012/0078004. There, lactide is reacted with methyl acetate and acetic acid. However, this process produces significant amounts of 2-acetoxypropionic acid. Yield and selectivity are very low, with much of the lactide being converted to dimers and other oligomers of lactic acid.

There is a need in the art to provide an inexpensive route to MAP and other esters of 2-acetoxyalkanoic acid.

This invention is a process for making a 2-acetoxyalkanonic acid ester.

In one aspect of the invention, the process comprises heating a mixture of an 3,6-dialkyl-1,4-dioxane-2,5-dione, in which the alkyl groups at the 3 and 6 position may be unsubstituted or inertly substituted, with an excess of acetate ester having the structure

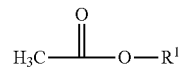

to a temperature of at least 150° C. under superatmospheric pressure in the presence of at least 0.1 mole per mole of the 3,6-dialkyl-1,4-dioxane-2,5-dione of an alkanol or phenol having the structure $R^1$—OH and in the presence of a transesterification catalyst to convert at least a portion of the 3,6-dialkyl-1,4-dioxane-2,5-dione to a 2-acetoxyalkanoic acid ester having the structure

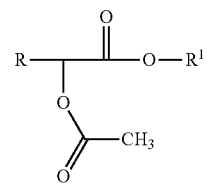

wherein R is an unsubstituted or inertly substituted alkyl group corresponding to the alkyl groups at the 3 and 6 positions of the starting 3,6-dialkyl-1,4-dioxane-2,5-dione and $R^1$ is alkyl (including linear, branched and cycloalkyl) or aryl.

This process produces the desired 2-acetoxyalkanonic acid ester in high yields. Conversion is often essentially quantitative and selectivity to the desired product is very high compared to the process described in US 2012/0078004.

In a second aspect of the invention, the process comprises heating a mixture of a poly(α-hydroxyalkanoic acid) having a number average degree of polymerization of at least 8 and a combined concentration of water and carboxyl groups of no greater than 2 moles/kg, with an excess of acetate ester having the structure

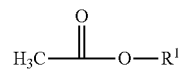

to a temperature of at least 150° C. under superatmospheric pressure in the presence of a transesterification catalyst to convert at least a portion of the poly(α-hydroxyalkanoic acid) to a 2-acetoxyalkanoic acid ester having the structure

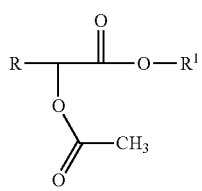

wherein R is an unsubstituted or inertly substituted alkyl group and $R^1$ is alkyl (including linear, branched and cycloalkyl) or aryl.

In the process of the first aspect of the invention, the starting 3,6-dialkyl-1,4-dioxane-2,5-dione can be represented by the structure

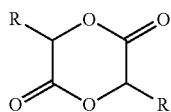

wherein each R is independently alkyl which may be unsubstituted or inertly substituted. R may be linear, branched or cyclic, and may have substituents that are inert (i.e., do not react) under the conditions of the process. Examples of such substituents include, for example, halogen, aryl, aryl ether and the like. Each R is preferably methyl, in which case the dione compound is lactide.

Each dione molecule contains two chiral centers, each of which exists in either the R- or the S-form. For purposes of this invention, either the R- or S-forms (or each) are useful. A lactide molecule, for example, can take one of three forms: 3S,6S-3,6-dimethyl-1,4-dioxane-2,5-dione (S,S-lactide), 3R,6R-3,6-dimethyl-1,4-dioxane-2,5-dione (R,S-lactide), or 3R,6S-3,6-dimethyl-1,4-dioxane-2,5-dione (R,S-lactide or meso-lactide). All of these are useful starting materials, as are mixtures of any two or more thereof.

The acetate ester corresponds to an ester of acetic acid with an alkanol or a phenolic compound (although it can be made using various methods). The alkyl acetate corresponds to the structure:

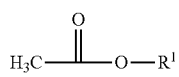

wherein $R^1$ is defined above. $R^1$ is preferably an unsubstituted alkyl group containing up to six carbon atoms, or phenyl. If alkyl, $R^1$ may be methyl, ethyl, n-propyl, i-propyl, n-butyl, sec-butyl, t-butyl, cyclohexyl, aryl, and the like. $R^1$ is most preferably methyl, n-butyl, or phenyl. Methyl is especially preferred because the lack of β-hydrogens limits unwanted side reactions during the pyrolysis of the methyl ester product (MAP) to form methyl acrylate.

The alcohol has the structure $R^1$—OH, in which the $R^1$ group is identical to the $R^1$ group of the acetate ester.

To perform the reaction, the acetate ester is combined with the starting dione at a mole ratio of at least 2:1. It is preferred to combine the starting dione with an excess of the acetate ester, as this helps to drive the equilibrium toward the desired product. A preferred molar ratio of acetate ester to α-hydroxyalkanoic acid ester is, at least 5:1, at least 10:1 or at least 20:1, and the mole ratio may be 100:1 or even higher.

At least 0.1, preferably at least 0.5, more preferably at least 0.8, and still more preferably at least 0.95, mole of alcohol or phenol is provided per mole of the starting dione compound. Lower amounts of the alcohol or phenol tend to favor higher selectivity but at the cost of reaction rate. It is generally unnecessary to provide any significant excess of the alcohol or phenol. A preferred amount of the alcohol or phenol therefore is up to 1.25 moles/mole of starting dione, and a more preferred amount is up to 1.05 moles/mole of starting dione. An especially preferred amount is 0.98 to 1.02 moles/mole of starting dione.

The transesterification catalyst is a material that catalyzes ester exchange reactions. Suitable transesterification catalysts are well-known in the art. Among these are strong Bronsted acids such as alkyl or aryl sulfonic acid compounds like para-toluene sulfonic acid, hydrochloric acid, sulfuric acid, phosphoric acid or oligomers of phosphoric acid. Strong Lewis acids are also suitable. These include, for example, tin chloride, tin oxide, dialkyl tin oxides, alkyltinalkoxides, alkyltincarboxylates, various titanium or aluminum compounds, boron trifluoride and the like.

The catalyst is used in catalytic quantities, which are typically 0.001 to 0.25 moles of the catalyst per mole of the starting dione.

It is not necessary to perform the reaction in a solvent or diluent, although one can be provided if desired. The solvent or diluent should not react under the conditions of the process. Examples of suitable solvents or diluents include hydrocarbons, ketones, chlorinated hydrocarbons, ethers, polyethers, and the like.

In the first aspect of the invention, water should be present in at most very small quantities, as water can engage in various reactions with the starting materials and reaction products to form acids and other unwanted species. It is preferred to provide the acetate ester, starting dione and starting alcohol in substantially anhydrous form, i.e., each containing less than 1% by weight water and each preferably containing less than 0.8% or less than 0.5% by weight water. Other sources of water preferably are excluded. Any atmosphere under which the reaction is performed preferably is substantially anhydrous. Overall, it is preferred that that water content in the reaction vessel during the reaction is maintained at below 1% by weight, more preferably below 0.5% by weight, and still more preferably below 0.15% by weight.

The reaction is performed at a temperature of at least 150° C. under superatmospheric pressure. A preferred temperature is at least 175° C. and still more preferred temperature is at least 190° C. A temperature above 230° C. is disadvantageous.

The aforementioned temperatures are greater than the boiling points of at least some of the starting materials. Therefore, the reaction is performed at superatmospheric pressure sufficient to maintain the starting materials as liquids during the reaction. A pressure of 10 to 60 atmospheres (1010 to 6060 kPa) is generally suitable, and a preferred pressure is 20 to 50 atmospheres (2020 to 5050 kPa).

The reaction can be performed continuously, semicontinuously or batch-wise in equipment capable of withstanding the operating temperature and pressure. Equipment which comes into contact with the hot reaction mixture and/or hot product mixture is preferably resistant to acids. Batch-type reactors include Parr reactors and other pressurized vessels. Continuous and semi-continuous reactors include pipe or tube reactors, loop reactors, continuously stirred tank reactors, and the like.

The reaction is continued until at least a portion of the starting materials are converted to the desired 2-acetoxyalkanoic acid ester. The reaction is an equilibrium reaction. Therefore, unless one or more of the products is removed as the reaction proceeds, the reaction mixture will reach an equilibrium prior to full conversion of the limiting starting material (typically, the dione or the alcohol) to product. Without removal of reaction products, the conversion of the limiting starting material will typically reach 50 to 80% if the reaction conditions are maintained for enough time. Higher conversions can be obtained when the acetate ester is used in larger excess.

In a batch process, a typical reaction time is 15 minutes to 10 hours. It is preferable to minimize reaction times to reduce the formation of unwanted by-products; in a preferred process, the reaction is discontinued when the conversion of the limiting starting material reaches 40 to 100%, especially 80 to 100% or even 90 to 100%, or when the reaction mixture reaches equilibrium.

A benefit of the inventive process is it is highly selective to the desired 2-acetoxyalkanonic acid ester. Selectivity of at least 40% or higher or 60% or higher to the desired product can be obtained easily with this invention. Selectivity is calculated by (a) determining the amount of starting dione consumed, (b) calculating the amount (B) of 2-acetoxyalkanonic acid ester that would have been produced if all the consumed dione had been converted to 2-acetoxyalkanonic acid ester, (c) determining the amount (C) of 2-acetoxyalkanonic acid ester produced, and (d) dividing C by B and multiplying by 100%. The main by-products of the reaction are oligomers of the α-hydroxyalkanoic acid, which may be in the form of esters.

Yield to the desired 2-acetoxyalkanonic acid ester are often at least 40%, based on the starting dione, and are often from 60% or higher. Yield is calculated as the amount of 2-acetoxyalkanoic acid ester produced divided by the amount that would be produced if all of the starting dione were converted to 2-acetoxyalkanoic acid ester.

The desired 2-acetoxyalkanonic acid ester is easily separated from the remaining components of the crude product mixture using distillation, crystallization, solvent extraction or other methods. Volatile components of the reaction mixture are easily flashed or otherwise distilled off. The 2-acetoxyalkanonic acid ester in most cases has a different boiling temperature and/or melting temperature than the starting materials. These differences in boiling and melting temperatures can be exploited as the basis for distillation and/or crystallization recovery processes.

Unreacted starting materials may be recovered, purified if necessary and recycled into the process. α-Hydroxyalkanoic acid oligomers (or esters of such oligomers) can be hydrolyzed back to the corresponding α-hydroxyalkanoic acid (or ester thereof), formed into the corresponding dione, and recycled into the process.

In the second aspect of the invention, a poly(α-hydroxyalkanoic acid) is used instead of lactide (or in combination with lactide) as the starting material. The starting poly(α-hydroxyalkanoic acid) may be a polymer of one or more α-hydroxyalkanoic acids such as glycolic acid, lactic acid, 2-hydroxylbutanoic acid and the like. Poly(lactic acid) is the preferred poly(α-hydroxyalkanoic acid).

The poly(α-hydroxyalkanoic acid) has a number average degree of polymerization of at least 8, preferably at least 10. Although the degree of polymerization can be any higher value, reaction rates tend to be low when the degree of polymerization becomes very high. Therefore, the number average degree of polymerization preferably is at most 100, at most 50, at most 25 or at most 20.

An advantage and surprising effect of using a poly(α-hydroxyalkanoic acid) as a starting material (compared to using lactide) is that the presence of water and carboxyl groups can be tolerated to a significant extent while retaining good yield and selectivity. Therefore, the starting poly(α-hydroxyalkanoic acid) can have a combined concentration of water and carboxyl groups of as much as 2 moles/kg. Preferred combined concentrations of water and carboxyl groups are preferably no greater than 1.75 moles/kg and still more preferably no greater than 1.5 moles/kg. The combined concentration of water and carboxyl groups may be at least 0.25 moles/kg, at least 0.5 moles/kg or at least 0.75 moles/kg.

Another advantage of using the poly(α-hydroxyalkanoic acid) of a starting material is the alkanol or phenol having the structure $R^1$—OH can be omitted, although with a certain loss of selectivity of the process. Therefore, in this second aspect of the invention, the alkanol or phenol can be omitted entirely. However, faster reaction rates, better selectivity and greater overall yield to product is seen when the alkanol or phenol is present. Therefore, in preferred embodiments of the second aspect of the invention, the alkanol or phenol is present in amounts as described before, the moles of alkanol or phenol being based on moles of α-hydroxyalkanoic acid repeating units in the starting poly(α-hydroxyalkanoic acid). Similarly, the starting acetate ester is provided in excess in relation to the moles of α-hydroxyalkanoic acid repeating units in the starting poly(α-hydroxyalkanoic acid).

Apart from the higher starting concentrations of water and carboxyl groups, and the optional omission of the alkanol and phenol, the conditions of the poly(α-hydroxyalkanoic acid) to 2-acetoxyalkanonic acid ester are as described above with respect to the use of a 3,6-dialkyl-1,4-dioxane-2,5-dione as the starting material. Reaction rates tend to be somewhat slower at equivalent conditions.

The process of the invention is particularly useful for forming 2-acetoxypropionic acid esters by reaction of lactide or a poly(lactic acid) with an acetate ester (preferably methyl acetate) and an alcohol (preferably methanol, which is optional but preferred when starting with poly(lactic acid)). The 2-acetoxypropionic acid ester product can by pyrolyzed to form acetic acid and an acrylate ester in which the ester group corresponds to the $R^1$ group in the starting materials. Pyrolysis can be performed by heating the 2-acetoxypropionic acid ester to a temperature of 400 to 600° C. under a non-oxidizing atmosphere. The acrylate ester is a useful monomer that can be polymerized or copolymerized to form acrylate polymers and copolymers. The acrylate ester can be hydrolyzed to form acrylic acid, which is itself a useful monomer, or can be converted to other acrylate monomers. The acetic acid can reacted with an alkanol or phenolic compound to regenerate the starting acetic ester, which can be recycled back into the process of this invention.

The process of the invention is also useful for producing butylacetoxypropionic acid. Butylacetoxypropionic acid is a useful starting material for an enzyme-catalyzed stereoselective deacylation process as described, for example, in WO 2014/045036.

The following examples are provided to illustrate the invention, and are not intended to limit the scope thereof. All parts and percentages are by weight unless otherwise indicated.

EXAMPLES 1-2

Example 1: 1 mole of lactide (containing less than 0.5 weight percent water), 25 moles of methyl acetate (containing about 0.5 weight percent water), 1 mole of methanol (containing about 0.08 weight percent water) and 0.05 mole of p-toluenesulfonic acid are charged to a Parr reactor. The reactor is pressurized to 90 pounds/square inch (about 620 kPa) with nitrogen to test for leaks, and then vented back to atmospheric pressure. The reactor and its contents are heated to 200° C. for 3 hours, during which time a pressure of 400 pounds/square inch (about 2750 kPa) developed in the reactor. The reaction mixture is then cooled to room temperature in the closed reactor. The reactor contents are removed and analyzed for residual lactide, the desired product (methyl 2-acetoxypropionic acid (MAP)), and lactic acid oligomers (including alkyl esters thereof) by gas chromatography with a flame ionization detector using commercially available standards. Conversion of methyl lactate is calculated from the amount of methyl lactate remaining in the reaction mixture. Selectivity to MAP is calculated from the measured amounts of MAP and oligomers. Yield to MAP is calculated as conversion multiplied by selectivity. Results are as indicated in the Table.

Example 2 is performed in the same manner, except the p-toluenesulfonic acid is replaced with an equivalent amount of tin chloride dihydrate. Results are indicated in the Table.

EXAMPLE 3

1 mole of lactide, 25 moles of butyl acetate, 2 mole of butanol, each containing less than 0.5 weight percent water) and 0.05 mole of tin chloride dihydrate are charged to a Parr reactor. The reactor is pressurized to 90 pounds/square inch (about 620 kPa) with nitrogen to test for leaks, and then vented back to atmospheric pressure. The reactor and its contents are heated to 200° C. for 3 hours, during which time a pressure of 100 pounds/square inch (about 690 kPa) developed in the reactor. The reaction mixture is then cooled to room temperature in the closed reactor. The reactor contents are removed and analyzed for residual lactide, the desired product (butyl 2-acetoxypropionic acid, BAP), and lactic acid oligomers (including alkyl esters thereof) by gas chromatography with a flame ionization detector using commercially available standards. Conversion of lactide is 99%. Selectivity to BAP is 57% and overall yield to desired product is 56%.

For comparison, Example 1 is repeated, replacing the methanol with an equal molar amount of acetic acid, and replacing the catalyst with 0.05 equivalents of nickel nitrate hexahydrate and 0.05 equivalents of nickel acetate tetrahydrate. The reaction is continued for six hours, during which time a pressure of 450 psi (about 3100 kPa) develops in the reactor. Results are reported in the Table as Comparative Sample A.

TABLE 1

| Designation | Reagents | Catalyst | Conversion of Lactide | Selectivity to MAP | Overall Yield to MAP (based on lactide) |
|---|---|---|---|---|---|
| Ex. 1 | Lactide, methyl acetate, methanol | p-TSA[1] | 100% | 42% | 42% |
| Ex. 2 | Lactide, methyl acetate, methanol | SnCl$_2$[1] | 100% | 66% | 66% |
| Ex 3 | Lactide, butyl acetate, butanol | SnCl$_2$[1] | 99 | 57 | 56 |
| Comp. Sample A | Lactide, methyl acetate, acetic acid | Ni(NO$_3$)$_2$, Ni(OAc)$_2$ | 80% | 14% | 11% |

[1]p-TSA is para-toluenesulfonic acid. SnCl$_2$ is tin chloride dehydrate. Ni(NO$_3$)$_2$ is nickel nitrate hexahydrate. Ni(OAc)$_2$ is nickel acetate tetrahydrate.

The conversion, selectivity and overall yield to MAP are extremely high in relation to prior art processes. In these experiments, the tin catalyst is more selective to MAP than the p-TSA catalyst. Use of the larger alcohol (butyl vs. methyl) results in slower rates (see example 2 vs. 3).

EXAMPLES 4-7

Example 4: One mole of poly(lactic acid) polymer [M$_n$=912 g/mol, degree of polymerization about 10.5], 25 moles of methyl acetate, and 0.05 mole of tin (II) chloride dihydrate are charged to a Parr reactor. The reactor is pressurized to 90 pounds/square inch (about 620 kPa) with nitrogen to test for leaks, and then vented back to atmospheric pressure. The reactor and its contents are heated to 200° C. for 3 hours, during which a pressure of 400 psi (2750 kPa) develops in the reactor. The reaction mixture is then cooled to room temperature in the closed reactor. The reactor contents are removed and analyzed for residual lactate, the desired product (MAP), and lactic acid oligomers (including alkyl esters thereof) by gas chromatography with a flame ionization detector using commercially available standards for the products. Results are indicated in Table 2.

Example 5 is performed in the same way as Example 4, except 2 moles of methanol are included in the reaction mixture. Results are as indicated in Table 2.

Example 6 is performed in the same way as Example 5, except the methyl acetate is replaced with an equivalent amount of n-butyl acetate and the methanol is replaced with an equivalent amount of butanol. During the reaction, the pressure increases to only about 100 psi (690 kPa). Results are as indicated in Table 2.

Example 7 is performed in the same way as Example 6, except 15 moles of butyl acetate are included in the reaction mixture. Results are as indicated in Table 2.

TABLE 2

| Designation | Reagents | Time (hr) | Conversion | Selectivity to product | Overall Yield to MAP/BAP |
|---|---|---|---|---|---|
| Ex. 4 | Poly(lactic acid) | t = 2 hr | 92% | 17% | 16% |
| | methyl acetate (25 mol) | t = 3.5 hr | 97% | 33% | 32% |
| Ex. 5 | Poly(lactic acid) | t = 2 hr | 96% | 29% | 28% |
| | methyl acetate (25 mol) methanol (2 mol) | t = 4 hr | 98% | 36% | 35% |
| Ex. 6 | Poly(lactic acid) | t = 2 hr | 79% | 6% | 5% |
| | n-butyl acetate (25 mol) n-butanol (2 mol) | t = 4 hr | 96% | 22% | 21% |
| Ex. 7 | Poly(lactic acid) | t = 2 | 84% | 6% | 5% |
| | n-butyl acetate (15 mol) n-butanol (2 mol) | t = 4 hr | 96% | 21% | 20% |

[1]SnCl$_2$ is tin chloride dihydrate.

Regardless of the absence or presence of exogenous alcohol, high conversions of the poly(lactic acid) are seen. Conversion is determined by converting the remaining poly (lactic acid) to lactide in the gas chromatography unit at 250° C. injector temperature, and measuring the amount of lactide produced. The amount of lactide produced is indicative of the amount of unreacted poly(lactic acid) in the sample. Selectivity and overall yield to product are higher when the alkanol is present, as in Examples 5 and 7. However, in none of these cases has the reaction reached a final equilibrium. A significant amount of acylated poly(lactic acid) oligomers are present in the product. Continuing the reaction will convert these oligomers to desired product and increase both selectivity and overall yields.

What is claimed is:

1. A process for making a 2-acetoxyalkanoic acid ester comprising heating a mixture consisting of a 3,6-dialkyl-1,4-dioxane-2,5-dione, in which the alkyl groups at the 3 and 6 position may be unsubstituted or substituted with substituents that do not react under the conditions of the process, an excess of acetate ester having the structure

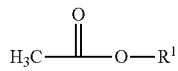

and at least 0.1 mole per mole of the 3,6-dialkyl-1,4-dioxane-2,5-dione of an alkanol or phenol having the structure $R^1$—OH to a temperature of at least 150° C. under superatmospheric pressure in a reaction vessel in the presence of a transesterification catalyst while maintaining the water content in the reaction vessel to below 0.5% by weight to convert at least a portion of the 3,6-dialkyl-1,4-dioxane-2,5-dione to a 2-acetoxyalkanoic acid ester having the structure

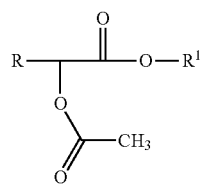

wherein R is an unsubstituted or inertly substituted alkyl group corresponding to the alkyl groups at the 3 and 6 positions of the starting 3,6-dialkyl-1,4-dioxane-2,5-dione and $R^1$ in each instance is alkyl or aryl, the process being characterized by a selectivity of at least 40% to the 2-acetoxyalkanoic acid ester and a yield of 2-acetoxyalkanoic acid ester of at least 40%, based on the starting amount of the 3,6-dialkyl-1,4-dioxane-2,5-dione; and wherein the transesterification catalyst is selected from the group consisting of an alkyl or aryl sulfonic acid compound, hydrochloric acid, sulfuric acid, phosphoric acid, an oligomer of phosphoric acid, tin chloride, tin oxide, a dialkyl tin oxide, an alkyltinalkoxide, an alkyltincarboxylate, and boron trifluoride.

2. The process of claim 1, wherein the 3,6-dialkyl-1,4-dioxane-2,5-dione is lactide.

3. The process of claim 1, wherein the mixture contains at least 0.8 mole per mole of the 3,6-dialkyl-1,4-dioxane-2,5-dione of an alkanol or phenol having the structure $R^1$—OH.

4. The process of claim 2, wherein the acetate ester is methyl acetate and the alkanol is methanol.

5. The process of claim 2, wherein the acetate ester is phenyl acetate and the phenol is phenol.

6. The process of claim 2, wherein the acetate ester is n-butyl acetate and the alkanol is n-butanol.

7. The process of claim 1, further comprising recovering the 2-acetoxyalkanoic acid ester.

8. The process of claim 7, wherein the 2-acetoxyalkanoic acid ester is recovered by crystallization or distillation.

9. The process of claim 1, wherein the conversion of the starting 3,6-dialkyl-1,4-dioxane-2,5-dione is at least 90%.

10. The process of claim 1, wherein the selectivity to the 2-acetoxyalkanoic acid ester is at least 60%.

11. The process of claim 1 wherein the transesterification catalyst is selected from the group consisting of para-toluene sulfonic acid and tin chloride.

* * * * *